United States Patent [19]
Maki et al.

[11] 4,333,908
[45] Jun. 8, 1982

[54] KIT FOR DETERMINING SILICA-ALUMINA CATALYST IN FUEL OIL

[75] Inventors: Hiroya Maki; Taketoshi Furusawa; Takeo Takaishi, all of Nagasaki, Japan

[73] Assignee: Mitsubishi-Jukogyo Kabushiki Kaisha, Japan

[21] Appl. No.: 221,195

[22] Filed: Dec. 29, 1980

[30] Foreign Application Priority Data

Jan. 14, 1980 [JP] Japan .............................. 55/1922[U]
Sep. 19, 1980 [JP] Japan ........................ 55/132245[U]

[51] Int. Cl.³ ...................... G01N 33/22; G01N 1/00
[52] U.S. Cl. ................................. 422/61; 23/230 R; 23/230 HC
[58] Field of Search ......... 422/61; 23/230 R, 230 HC

[56] References Cited
U.S. PATENT DOCUMENTS

| | | | |
|---|---|---|---|
| 3,528,775 | 9/1970 | O'Hara | 23/230 HC |
| 4,195,059 | 3/1980 | Whitcher | 422/61 |
| 4,203,725 | 5/1980 | Snowden | 23/230 HC |
| 4,238,197 | 12/1980 | Eisentraut | 422/61 X |

OTHER PUBLICATIONS

"Hackh's Chemical Dictionary", Julius Grant, Ed., p. 274, Fourth Edition, McGraw-Hill, New York, 1969.

Primary Examiner—Sidney Marantz
Attorney, Agent, or Firm—McGlew & Tuttle

[57] ABSTRACT

An analysis kit for fuel oil to determine its silica-alumina catalyst component content, comprises a plurality of syringes for sampling fuel oil, sample containers for holding the sampled oil, an organic solvent for dissolving the oil in one of the containers, a filter for the solution of the sample in the organic solvent, a reagent for dissolving a catalyst component in the filtration residue formed by the filter, a measuring cylinder to contain the solution formed by the reagent, purified water for diluting the solution in the cylinder to a predetermined volume, color-producing reagents to be added to the solution adjusted with the purified water, a unit for comparing the color developed by the color-producing reagents with colors of known standards, and a portable box accommodating all of the above-mentioned items and supplies.

4 Claims, 6 Drawing Figures

KIT FOR DETERMINING SILICA-ALUMINA CATALYST IN FUEL OIL

FIELD AND BACKGROUND OF THE INVENTION

This invention relates to a kit for simply analyzing fuel oil for its catalyst component content.

Fuel oil for marine engines has commonly been a mixture of light gas oil and long and short residuums from atmospheric and vacuum distillations, respectively. However, in order to meet growing demand for light gas oil and save the fuel cost, there is an increasing tendency in the art to squeeze out an additional percentage of light oil from the long and short residuums by thermal or catalytic cracking or other technique and then mix the thickened residue with light gas oil or the like as fuel for marine engines.

The mixed fuel thus formed is high in specific gravity and viscosity, with by far the greater carbon residue than the ordinary heavy fuel oil C.

The residue after the extraction of light gas oil by catalytic cracking is generally known as fluid catalytic cracking (FCC) oil. It contains hard microspheroids of a silica-alumina catalyst, ranging in particle size from 5 to 80μ, as the catalyst for catalytic cracking. The fuel oil containing such hard particles is believed responsible for the unusual wear of piston rings and cylinder liners of diesel engines. There are instances in which fuels incorporating FCC oils with Si contents of 300 to 3000 ppm caused rapid wear of the rings and liners in diesel engines. If this premature wear is to be avoided, it will be necessary to know if any FCC oil is incorporated in the fuel and, if so, remove it or reject the fuel oil.

A conventional practice for analyzing fuel oil for the presence of the silica-alumina catalyst in the FCC oil as fuel has been to ash the questionable fuel oil once, dissolve the ash in a solvent, and subject the resulting solution to a colorimetric analysis for silica. The fuel oil ashing is conducted in conformity with the procedure of Japanese Industrial Standards K-2272 (Testing Method for Determination of Ash Contents in Crude Oils and Petroleum Products). The procedure consists in gradually carbonizing the fuel by weak heating until the oil ceases to give off any more volatile matter, and then reducing the resultant to ash by heating at about 800° C. Thus, complete ashing takes about two days, or too much time to meet field requirements.

In order to eliminate the disadvantage, we have already proposed in Japanese Patent Application No. 13865/1979 a method for field analysis to determine the catalyst component content in fuel oil in a simple and quick way. The previous invention was perfected with the view to analyzing the fuel oil to be supplied to a ship at any port of call for her engines conveniently and promptly to see if it contains the FCC oil and avoiding the use of any fuel oil containing the same and thereby preventing troubles of the diesel engines and the like. To attain the end, that invention comprises dissolving a sample amount of fuel oil in an organic solvent, filtering the solution and separating out the residue, i.e., the silica-alumina catalyst, dissolving its main component silica into fluoric acid, and then subjecting the resulting solution to colorimetric determination of its Si ion content. Without the need of ashing the residue, the method of the invention is advantageous over the conventional technique in that it permits simpler and quicker determination of the silica content and easier detection of the FCC oil present in the fuel. The method is, therefore, effectively applicable to the evaluation of a given fuel (usually fuel oil C), its adequacy or inadequacy for given thermal engines, such as diesels or boilers.

However, there has been no equipment available for the field analysis in conformity with the method of the invention.

SUMMARY OF THE INVENTION

It is an object of this invention to provide a kit for field analysis whereby a fuel oil can be simply and quickly analyzed for its catalyst component content. The kit according to the invention consists of a small, portable box accommodating a collection of implements and supplies, including syringes, sample containers, organic solvent, filter means, catalyst-component-dissolving reagent, measuring cylinder, purified water, color-producing reagents, and standard $SiO_2$ color solutions. The kit permits one having little knowledge of chemistry to determine by a simplified procedure the content of the catalyst component in a given fuel oil.

Another object of the invention is to provide an analysis kit adapted for an improved procedure for color comparison, whereby the lower limit of the $SiO_2$ determination can be lowered from the order of 50 ppm down to the order of 10 ppm. The kit consists of a small, portable box accommodating a collection of implements and supplies, including syringes, sample containers, organic solvent, filter means, catalyst-component-dissolving reagent, measuring cylinders, purified water, color-producing reagents, and color comparison unit. The kit enables one having little skill in the art to determine the catalyst component content of a given fuel oil by a simple procedure.

The kit according to the invention can effectively be used to evaluate a given fuel oil (usually heavy fuel oil C), whether it is unsuitable for given thermal engines, such as diesels or boilers.

These and other objects, features, and advantages of the invention will become more obvious from the following detailed description taken in conjunction with the accompanying drawings.

DESCRIPTION OF THE PREFERRED EMBODIMENTS

Figure 1:
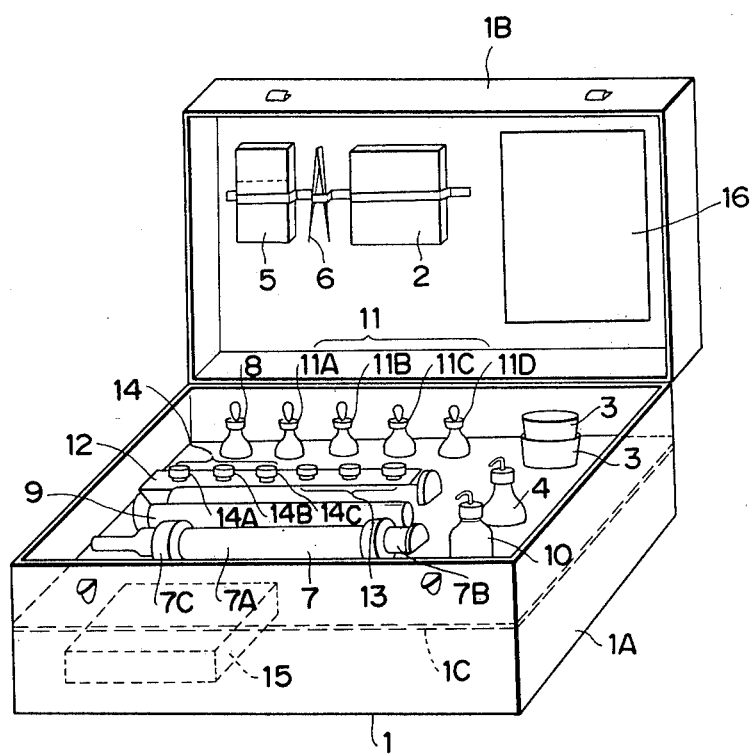
FIG. 1 is a perspective view of a first embodiment of the simplified analysis kit according to the invention.

Referring now to FIG. 1, there is shown a portable, wooden or plastics box 1 measuring, e.g., 250 mm long, 350 mm wide, and 140 mm high. It consists of a main box body 1A, a cover 1B openably hinged to the box body, and a partition plate 1C horizontally secured about halfway up the body.

The numeral 2 designates a set of 15 syringes, e.g., made of polyethylene resin, having a capacity of 2.5 ml each for fuel oil sampling. The syringes are packed in a small cardboard case and held inside the cover 1B.

Sample containers 3, e.g., of polyethylene resin, about 70 mm across and about 80 mm high, for holding the fuel oil samples transferred by means of the syringes 2 are placed in the box body 1A.

Also contained in the box body 1A is a washing bottle 4, e.g., of polyethylene resin, having a capacity of about 250 ml. It is filled with an organic solvent (e.g., benzene) for dissolving the fuel oil in each of the sample containers 3.

The numeral 5 indicates a filter medium to be used in filtering the test solution of a fuel oil in the organic solvent. It is of a membrane type of ethylene tetrafluoride (e.g., the product of Sumitomo Electric Industries, Ltd. marketed under the trade designation "Fluoropore filter"). Packed in a small cardboard case, the medium 5 is carried inside the cover 1B.

Indicated at 6 is a pair of tweezers also carried by the cover 1B for use in fitting the filter medium in and removing it from a filter now to be described.

The filter 7 filtrates the test solution of the oil sample in the organic solvent and separates an objective catalyst component by means of the filter medium 5 to be set inside. Here in this embodiment the filter is shown as of an injector type for rapid filtration comprising a cylinder 7A, a piston 7B, and a section 7C provided under the cylinder 7A and in which the filter medium 5 is to be fitted. The filter body is made, e.g., of polyethylene resin and measures 240 mm in overall length and 36 mm in diameter of the cylinder. The filter 7, accommodated in the box body 1A, forms a filter means in combination with the filter medium 5 and the tweezers 6.

A container 8 holds a reagent, or a fluoric acid solution, for dissolving the catalytic component in the residue of filtration through the filter medium 5. It is a small-mouthed bottle, e.g., of polyethylene resin, 47 mm across and 97 mm high, and has a capacity of 100 ml. The bottle, placed in the box body 1A, is equipped with a dropper made of polyethylene resin capable of taking up 2 to 5 ml of a liquid, the dropper being inserted through the upper cap made of the bottle.

Inside the box body 1A is also laid a measuring cylinder 9 to receive the solution of the oil sample in the reagent 8. It is made, e.g., of polyethylene resin and has a diameter of 30 mm and a height of 210 mm, with a capacity of about 200 ml.

The numeral 10 indicates a washing bottle containing purified water for diluting the solution in the measuring cylinder 9 to a predetermined quantity. Made of polyethylene resin, e.g., it has a capacity of about 250 ml. The bottle is placed inside the box body 1A.

A plurality of color-producing reagents, collectively indicated at 11, are held by containers similar to the container of the reagent 8 in material, size, and design. The container 11A holds an HF-shielding reagent, 11B a color-producing reagent, 11C an interfering-ion-shielding reagent, and 11D a coloring-reducing reagent. All the containers are housed in the box body 1A.

For the convenience of color comparison, a container stand 12 is set inside the box body 1A. The numerals 13 and 14 are groups of containers, respectively, for the colored and standard solutions for color comparison. All the containers are of the same material and same size, e.g., of styrol resin and 32 mm in diameter and 85 mm in height, with a capacity of 50 ml each. They are supported by the stand 12.

The sample containers 3, organic solvent, container 4, filter 7, catalyst-component-dissolving reagent container 8, measuring cylinder 9, purified water container 10, color-producing reagent containers 11, and container stand 12 are all kept in place through corresponding holes formed in the horizontal partition plate 1C inside the box body 1A.

In the space between the partition plate 1C and the bottom of the box body is accommodated a spare reagent case 15, e.g., of plastics, measuring approximately 100 mm by 200 mm by 50 mm.

Attached to the inner side of the box cover 1B is an instruction manual 16 for the handling of this kit.

The construction and contents of the simplified analysis kit for the indentification of a catalyst component in fuel oil in accordance with the invention have so far been described with reference to FIG. 1. Now, the procedures for preparing the reagents and standard color solutions for the kit will be described below.

I. REAGENTS

(1) Reagent 8 for dissolving objective catalyst component

A 2-ml portion of hydrofluoric acid (a 46 wt% HF solution, chemical grade) is taken up by a measuring pipette and is diluted with purified water to a total volume of 100 ml.

(2) HF-shielding reagent 11A

To a solution of 16.7 g of special grade aluminum sulfate in about 70 ml of purified water is added 10 ml of sulfuric acid. The total quantity is increased to 100 ml by the addition of purified water.

(3) Color-producing reagent 11B

Ten grams of special grade ammonium molybdate is added to about 70 ml of purified water and is dissolved by heating at about 60° C. with stirring. Upon cooling, the solution is diluted with purified water to a total quantity of 100 ml.

(4) Interfering-ion-shielding reagent 11C

Twenty grams of special grade citric acid is dissolved in about 70 ml of purified water, and again purified water is added to give a total quantity of 100 ml.

(5) Coloring-reducing reagent 11D

One gram of special grade tin chloride is dissolved in 5 ml of hydrochloric acid, and the total quantity is increased to 100 ml with purified water.

II. STANDARD COLOR SOLUTIONS 14

(a) Into a small amount of purified water is introduced 29.65 g of special grade cobalt chloride ($CoCl_2.6H_2O$) and is dissolved by adding 5 ml of hydrochloric acid. The total amount is diluted with purified water to 500 ml.

(b) With the addition of 5 ml of hydrochloric acid, 124.84 g of special grade copper sulfate ($CuSO_4.5H_2O$) in a small amount of purified water is dissolved. The total quantity is increased to 500 ml with purified water.

The cobalt chloride solution and the copper sulfate solution thus prepared are mixed in combinations of varied proportions as given in Table 1, each mixture being diluted to a total quantity of 40 ml. The resulting solutions are, e.g., standard color solutions 14A, 14B, and 14C for 50 ppm, 100 ppm, and 200 ppm $SiO_2$, respectively. These solutions 14A to 14C are compared with the colored solutions in the containers 13 to determine the concentration of the objective component in the test solution. Although the standard color solutions in this embodiments are specified for the $SiO_2$ concentrations of 50, 100, and 200 ppm, this is not a limitation to this invention but solutions for various other concentrations can be made by simply varying the proportions of the cobalt chloride solution (a) and the copper sulfate solution (b) in the mixed solutions.

TABLE 1

| Standard solution No. | For $SiO_2$ (ppm) | Mixed solution Cobalt chloride(a) | Copper sulfate(b) |
| --- | --- | --- | --- |
| 14A | 50 | 3 ml | 7.5 ml |
| 14B | 100 | 6 ml | 15.0 ml |
| 14C | 200 | 9 ml | 30.0 ml |

The actual procedure for analyzing fuel oil by means of the kit according to the invention will now be explained.

First, one milliliter of a fuel oil to be analyzed is taken up with the measuring cylinder 2 and is introduced into the sample container 3. From the washing bottle 4 about 100 ml of an organic solvent, e.g., benzene, is transferred into the container 3. The container is then placed in a bath of hot water at about 60°–70° C. with intermittent stirring of the contents for about 5 minutes so as to dissolve the fuel oil.

Next, the piston 7B of the filter 7, e.g., of the injector type, is withdrawn and the section 7C below the cylinder 7A for fitting the filter medium is disconnected from the cylinder by turning it anticlockwise relative to the latter. One sheet of the filter medium 5 is picked out of the case with the tweezers 6 and fitted in place within the section 7C and the medium-loaded section is attached back to the lower part of the cylinder 7A. The filter is now ready for filtration.

Following the completion of these preparations, the test solution is transferred from the sample container 3 to the cylinder 7A. At this time, the washing bottle 4 is used to wash away every residual drop of the solution with benzene.

The piston 7B is then inserted into the cylinder 7A. With an air vent (not shown) formed in the rear center of the piston closed with a finger, the piston is further forced inward to filter the test solution. After the passage of the solution through the filter medium, the piston 7B is slowly pulled off, with the center air vent uncovered, from the cylinder 7A. Again using the washing bottle 4, the inner wall of the cylinder 7A is washed with a small amount of benzene. In the same manner as above described, the piston 7B is reintroduced into the cylinder 7A and filtration is again performed.

The washing procedure is repeated twice or thrice and is discontinued when the benzene in the filtrate has become substantially transparent.

From the cylinder 7A the piston 7B is slowly pulled off, and the benzene is also removed by air drying from the cylinder. Then, 5 ml of the catalyst-component-dissolving reagent 8 is taken out of the bottle with the pipette fitted to its cap and is added to the catalyst component separated by filtration and left on the filter medium. The mixture is allowed to stand for 5–7 minutes in the cylinder 7A to dissolve the catalyst component.

The resulting solution is transferred from the cylinder 7A to the measuring cylinder 9. Using the washing bottle 10 containing purified water, the inner wall of the cylinder 7A is washed with a small amount of purified water. The washings too are introduced into the measuring cylinder 9.

Next, 2 ml of the HF-shielding reagent 11A is pipetted into the measuring cylinder 9, and the total quantity of the charge inside the cylinder is increased with the purified water from the washing bottle 10 to 50 ml.

With the addition of 5 ml of the color-producing reagent 11B by pipetting to the measuring cylinder 9, the total charge is allowed to stand for 2–3 minutes to develop the color of molybdenum yellow.

Further, 2 ml of the interfering-ion-shielding reagent 11C and then 1 ml of the coloring-reducing reagent 11D are introduced, in succession, into the measuring cylinder 9.

After standing for 10–15 minutes, the colored solution is transferred from the cylinder 9 to the color-comparing containers 13, and then the color is visually compared with those of the standard color solutions 14 in the containers held upright by the container stand 12 to determine the concentration of the objective catalyst component.

The method of color comparison employed here for colorimetric determination is the so-called molybdenum blue method, in which an ammonium molybdate solution is added to the sample solution to develop molybdenum yellow, and a tin chloride solution is added as a reducing agent to the mixed solution to produce a blue color, and then the color is compared with the colors of known standards. In this way the test solution is analyzed for Si ions, and the $SiO_2$ quantity is determined on the basis of the comparison with the standard color solutions.

In the foregoing description the analysis has been directed to the determination of Si ions as representative of the silica-alumina catalyst, because the catalyst used was of the silica-alumina system and the catalyst available for the model procedure was of a composition largely dominated by silica, viz., 68.4 wt% $SiO_2$ as compared with 9.6 wt% $Al_2O_3$.

The method of the invention using the aforedescribed embodiment of the analysis kit will be compared with other analytical methods of the prior art in Comparative Example 1 below.

COMPARATIVE EXAMPLE 1

In this series of comparative experiments the standard color solutions used for color comparison purposes were prepared for three different concentrations of 50, 100, and 200 ppm. This permitted the determination of the $SiO_2$ concentrations in oil samples by presenting unknown colors beside a relatively broad comparison field.

Table 2 summarizes the results of analyses made of test oils for their $SiO_2$ concentrations by a conventional method (that involves ashing and the use of an emission photometer), an improved method (dissolution in benzene, separation by filtration, and the use of an emission photometer), and the method of the invention using the simplified analysis kit (dissolution in benzene, separation by filtration, and the use of standard color solutions).

TABLE 2

| Analytical method | Analytical values of SiO₂ in ppm |  |  |  |  |
|---|---|---|---|---|---|
|  | Fuel oil analyzed |  |  |  |  |
|  | No. 1 | No. 2 | No. 3 | No. 4 | No. 5 |
| Conventional | 94.1 | — | — | — | 121.5 |
| Improved | 92.8 | 8.3 | 16.3 | 10.7 | 130.7 |
| This invention | 50< ≦100 | <50 | <50 | <50 | 100≦ <200 |

In the table, the test fuel oil No. 1 contains FCC oil and No. 2 is heavy fuel oil C. It will be seen that there is a clear distinction between the two in the $SiO_2$ content.

The rest of test oils are from unknown processes, but it appears very likely that No. 5 is an FCC-oil-containing fuel oil.

A comparison of the analytical values obtained by use of the simplified analysis kit according to the invention with those by the conventional and improved methods of the prior art indicates relatively good reproducibility of the method of the invention, with the $SiO_2$ concentrations in all of the oils tested being well within the range of concentrations determined with the kit of the invention.

Also, according to the intensity of color developed by a test solution, it is quite possible to judge to which standard color solution is the sample closer in value than the rest.

Figure 2:
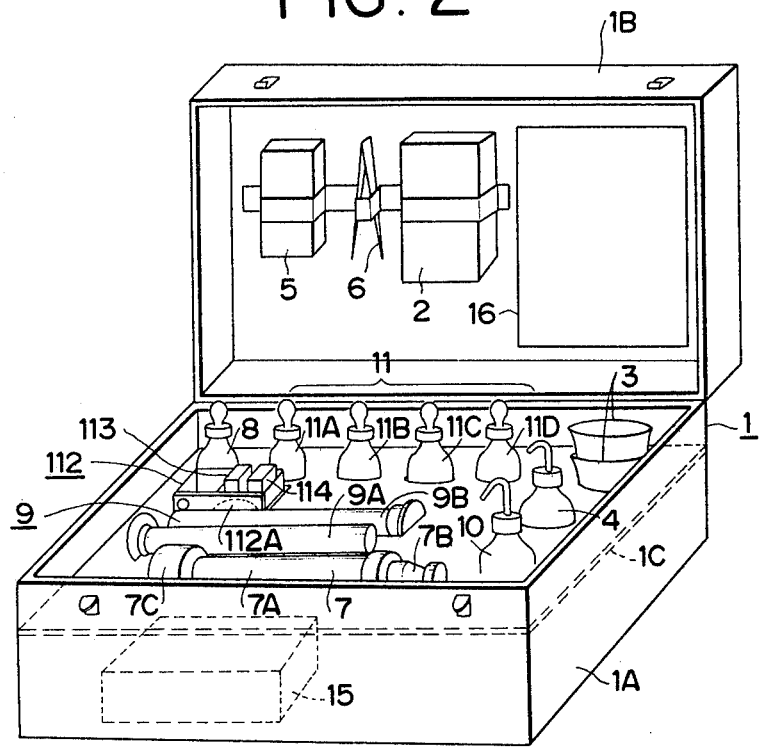
FIG. 2 is a perspective view of a second embodiment of the invention.
Figure 3:
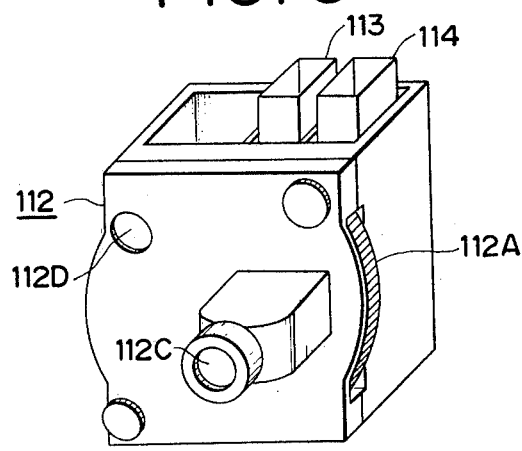
FIG. 3 is a detailed view of the color comparison unit 112 in FIG. 2.
Figure 4:
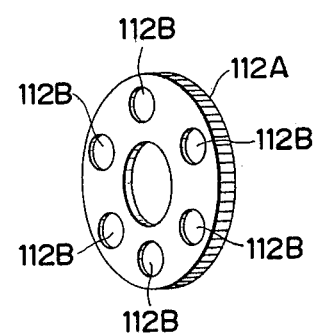
FIG. 4 is a detailed view of the standard color dial 112A in FIG. 3.

FIGS. 2 to 4 illustrate another embodiment of the invention. In these figures the numeral 112 indicates a color comparison unit for the comparison of color intensities, e.g., a reflection-prism color comparator (mfd. by Toyo Scientific Ind. Co.), as better shown in FIG. 3 and in a detailed view of a part in FIG. 4. It comprises a case, a standard color dial 112A carrying standard colors 112B, an eyehole attachment to the case, and a concentration-indicating hole 112D. This unit is housed in the box body 1A. Rectangular comparison containers 113 and 114, respectively, for the test solution and the control solution are held upright in the color comparison unit 112. They are formed, e.g., of styrol resin, and measure 86 mm by 16 mm by 25 mm, with a capacity of 20 ml each.

The remainder of component parts are the same as those of the first embodiment illustrated in FIG. 1, and therefore they are likewise numbered for reference and the description is not repeated here. An additional exception is that this second embodiment employs two measuring cylinders 9A and 9B instead of one, the cylinders being both contained in the box body 1A.

Thus, the sample containers 3, organic solvent container 4, filter 7, catalyst-component-dissolving reagent container 8, measuring cylinders 9, purified water container 10, color-producing reagent containers 11, and color comparison unit 112 are all kept in place through corresponding holes formed in the horizontal partition plate 1C inside the box body 1A.

The procedures for preparing the reagents are the same as those for the preceding embodiment, and therefore the description is omitted except that the set of standard colors 112B, a feature not incorporated in the first embodiment, will be explained below.

STANDARD COLORS 112B

Figure 5:
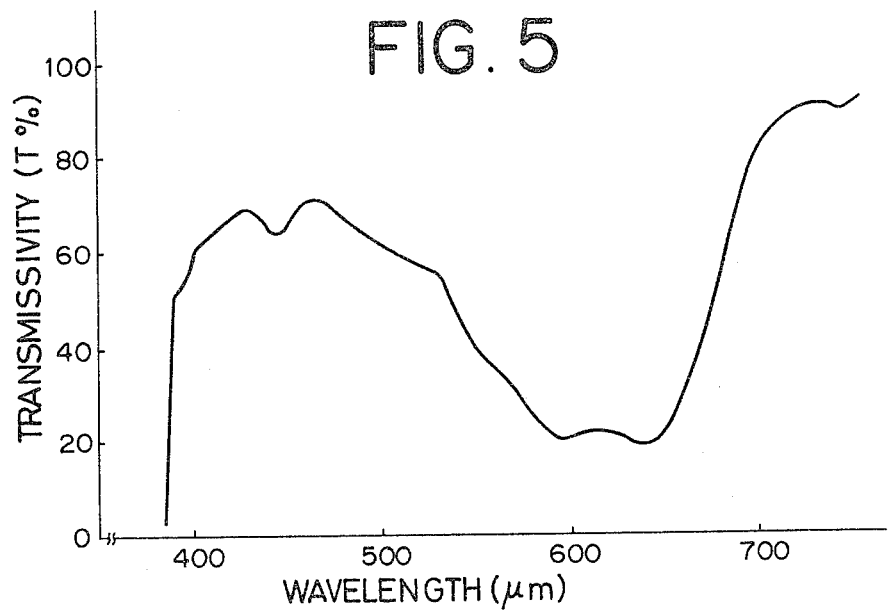
FIG. 5 is a graphic representation of typical transmissivity characteristics of the standard colors 112B to be used in accordance with the invention.
Figure 6:
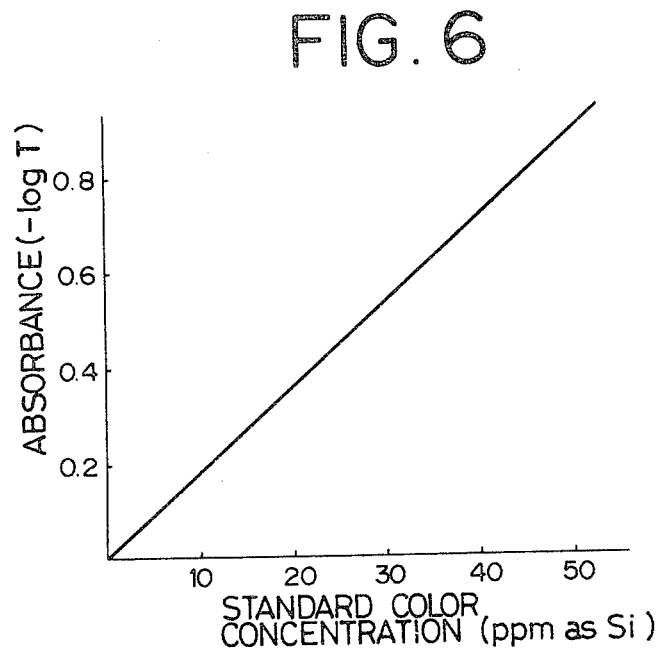
FIG. 6 is a graph illustrating the relationship between the standard color concentration and absorbance at the wavelength of 640 μm.

Standard colors 112B for 5, 10, 20, 30, 40, and 50 ppm of Si ions, preadjusted, e.g., with colored acrylic resin or color glass, are set in the standard color dial 112A turnably installed inside the color comparison unit 112. Those colors are compared with the color intensity of the colored solution to determine the concentration of the objective constituent in the solution. In FIG. 5 are plotted typical transmissivity (T %) characteristics of the standard colors 112B versus wavelengths (in $\mu$m), and FIG. 6 graphically represents the relation between the standard color concentration (in terms of Si in ppm) and the absorbance ($-\log T$) at the wavelength of 640 $\mu$m.

Analysis of fuel oil with this kit of the second embodiment is made in the following way. The sequence of procedures up to the color comparison are the same as that already explained in connection with the first embodiment. Then, 2 ml of the interfering-ion-shielding reagent 11C is additionally pipetted into the measuring cylinder 9A, and 1 ml of the coloring-reducing reagent 11D into the cylinder 9B.

After standing for 10-15 minutes, the colored solution in the measuring cylinder 9A is transferred to the rectangular comparison container 113 for the test solution, and the colored solution (i.e., the catalyst-component-dissolving reagent 8) in the cylinder 9B is transferred to the container 114 for the control solution. The both cylinders are held upright in place within the color comparison unit 112. The operator, while observing the inside against natural color through the eyehole attachment 112C, turns the standard color dial 112A and visually compares the respective standard colors 112B with each colored solution and then reads out the numerical values from the concentration-indicating hole 112D, thus determining the objective concentration.

The method of color comparison employed here for colorimetric determination is the so-called molybdenum blue method, in which an ammonium molybdate solution is added to the sample solution to develop molybdenum yellow, and a stannous chloride solution is added as a reducing agent to the mixed solution to produce a blue color, and then the color is compared with the colors of known standards. In this way the test solution is analyzed for Si ions, and the Si quantity is determined by use of the standard color dial 112A.

The method of the invention using this second embodiment of the analysis kit will be compared with other analytical methods of the prior art in Comparative Example 2 below.

COMPARATIVE EXAMPLE 2

In this series of comparative experiments the standard color dial for color comparison used six different standard colors for concentrations of 5, 10, 20, 30, 40, and 50 ppm. This permitted the determination of the Si ion concentrations in oil samples by presenting unknown colors beside a relatively broad comparison field.

Table 3 shows the results of analyses made of test oils for their $SiO_2$ concentrations in the manner similar to the preceding Example, by a conventional method (that involves ashing and the use of an emission photometer), an improved method (dissolution in benzene, separation by filtration, and the use of an emission photometer), and the method of the invention using the simplified analysis kit (dissolution in benzene, separation by filtration, and the use of the color comparison unit).

TABLE 3

| Analytical method | Analytical values of Si in ppm | | | | |
|---|---|---|---|---|---|
| | Fuel oil analyzed | | | | |
| | No. 1 | No. 2 | No. 3 | No. 4 | No. 5 |
| Conventional | 44.0 | — | — | — | 56.8 |
| Improved | 43.0 | 3.9 | 7.6 | 5.6 | 61.1 |
| This invention | 30< <40 | <5 | 5< <10 | 5 | <50 |

In the table, the test fuel oil No. 1 contains FCC oil and No. 2 is heavy fuel oil C. It will be seen that there is a clear distinction between the two in the Si ion content.

The rest of test oils are from unknown processes, but it appears very likely that No. 5 is an FCC-oil-containing fuel oil.

A comparison of the analytical values obtained by use of the simplified analysis kit according to this invention with those by the conventional and improved methods of the prior art indicates relatively good reproducibility of the method of the invention, with the Si ion concentrations in all of the oils tested being well within the range of concentrations determined with the kit of the invention.

Also, according to the intensity of color developed by a test solution, it is quite possible to judge to which standard color is the sample closer in value than the rest.

As will be obvious from the analytical values given above, the simplified analysis kit according to the invention is useful for field analysis and is very effective in conveniently determining whether a given fuel oil contains the objectionable FCC oil or not.

The present invention offers the following advantages:

(1) The kit according to the invention for simplified analysis of fuel oil for its catalyst component content comprises means for sampling the fuel oil to be analyzed, means for dissolving the fuel oil sampled by the preceding means, means for filtering the oil dissolved by the above means, means for dissolving the catalyst component in the residue from filtration by the above means, and means for colorimetrically analyzing the residue solution for the Si ion content of the catalyst component, all contained in a portable box. The kit is, therefore, compact in design, light in weight, and is handy for portable use.

The kit is easy to handle for the color comparison and determination use, and permits one not skilled in the art to do field analysis easily and promptly to a great advantage.

(2) As regards the preparations for analysis, it is only necessary to dissolve a fuel oil sample in an organic solvent and separate the residue by filtration. Consequently, this method takes but one hour or so for the residue extration whereas the prior art method requires about two full days.

(3) Mere analysis of fuel oil for its Si ion content gives an indication of whether the particular fuel contains the FCC oil, that is, whether it is unsuitable for use as fuel or not.

(4) The presence of the FCC oil being detectable, it is possible for a ship's crew or the like to reject the fuel oil containing it so as to prevent troubles of their diesel engines or the like.

(5) With the embodiment illustrated in FIGS. 2 to 4, determination of Si ion contents down to the range of 5–10 ppm in test oils is possible. This means that the kit allows analyses to be made with a high precision to determine such low concentrations of the objective catalyst component.

We claim:

1. An analytical kit for fuel oil to determine a silica-alumina catalyst component contained therein, which comprises a plurality of syringes for sampling fuel oil, sample containers for holding the sampled oil, an organic solvent for dissolving said oil in one of said containers, filter means for the solution of said oil in said organic solvent, a reagent for dissolving a catalyst component in the filtration residue formed by said filter means, a measuring cylinder to contain the solution formed by said reagent, purified water for diluting said solution in said cylinder to a predetermined volume, color-producing reagents to be added to said solution adjusted with said purified water, means for comparing the color developed by said color-producing reagents with colors of known standards, and a portable box accommodating all of said means and supplies.

2. An analytical kit according to claim 1, wherein said means for comparing the color developed by said color-producing reagents with colors of known standards is a set of standard color solutions.

3. An analytical kit according to claim 1, wherein said means for comparing the color developed by said color-producing reagents with colors of known standards is a color comparison unit.

4. An analytical kit according to claim 2 or 3 wherein: the catalyst dissolving reagent is a hydrofluoric acid solution; and the color-producing reagents include ammonium molybdate solution, an HF-shielding reagent, and interfering-ion-shielding reagent and a coloring-reducing agent.

* * * * *